United States Patent [19]

Inoue

[11] Patent Number: 4,561,214

[45] Date of Patent: * Dec. 31, 1985

[54] ABRADING TOOL

[75] Inventor: Kiyoshi Inoue, Tokyo, Japan

[73] Assignee: Inoue-Japax Research Incorporated, Kanagawa, Japan

[*] Notice: The portion of the term of this patent subsequent to Jan. 4, 2000 has been disclaimed.

[21] Appl. No.: 355,301

[22] Filed: Mar. 5, 1982

Related U.S. Application Data

[63] Continuation of Ser. No. 26,775, Apr. 3, 1979, abandoned.

[30] Foreign Application Priority Data

| Oct. 12, 1978 | [JP] | Japan | 53-125451 |
| Oct. 18, 1978 | [JP] | Japan | 53-128847 |
| Oct. 21, 1978 | [JP] | Japan | 53-130195 |
| Nov. 8, 1978 | [JP] | Japan | 53-136762 |
| Nov. 17, 1978 | [JP] | Japan | 53-142558 |
| Nov. 17, 1978 | [JP] | Japan | 53-142559 |
| Nov. 21, 1978 | [JP] | Japan | 53-144747 |
| Nov. 22, 1978 | [JP] | Japan | 53-144703 |
| Nov. 22, 1978 | [JP] | Japan | 53-144704 |
| Dec. 2, 1978 | [JP] | Japan | 53-149826 |
| Dec. 27, 1978 | [JP] | Japan | 53-160114 |
| Mar. 24, 1979 | [JP] | Japan | 54-34847 |

[51] Int. Cl.$^4$ .......................................... B24B 49/16
[52] U.S. Cl. .................................... 51/165 R; 51/336; 219/69 M; 15/104.14; 433/125
[58] Field of Search .................. 51/330-334, 51/336, 165 R; 15/104.14, 104.18, 159 A, 197, 198, 200; 433/125; 219/69 M

[56] References Cited

U.S. PATENT DOCUMENTS

| 564,497 | 7/1896 | Babis | 15/159 A |
| 1,040,808 | 10/1912 | Stork | 15/198 |
| 1,199,148 | 9/1916 | Bemis | 15/200 |
| 1,510,157 | 9/1924 | Pemberton | 15/198 |
| 1,694,636 | 12/1928 | Barker | 15/159 A |
| 2,608,034 | 8/1952 | Fromson | 51/336 |
| 2,608,816 | 9/1952 | Lembke | 51/336 |
| 3,383,727 | 5/1968 | Hanson | 15/104.4 |
| 3,696,563 | 10/1972 | Rands | 51/332 |
| 3,871,139 | 3/1975 | Rands | 51/334 |
| 3,906,681 | 9/1975 | Seidel | 51/165.92 |
| 3,952,458 | 4/1976 | Tomita | 51/165.77 |
| 4,367,389 | 1/1983 | Inoue | 51/334 |

FOREIGN PATENT DOCUMENTS

2051680 4/1972 Fed. Rep. of Germany ... 51/165.92

Primary Examiner—Harold D. Whitehead
Attorney, Agent, or Firm—Karl F. Ross; Herbert Dubno

[57] ABSTRACT

An abrading tool for any grinding, lapping, polishing or burnishing purpose (e.g. dental applications) has a rotary holder whose shank can be rotated (e.g. in a chuck connected to a motor) and a plurality of angularly equispaced elongate pieces projecting axially from the holder. The pieces carry abrasive over at least part of their lengths and collectively form a forwardly converging body of revolution about the axis (in a rest position) and the generatrices of this body serve to impact against and abrade the surface to be treated upon rotation of the tool.

15 Claims, 46 Drawing Figures

ABRADING TOOL

This is a continuation of application Ser. No. 026,775, filed Apr. 3, 1979, now abandoned.

FIELD OF THE INVENTION

The present invention relates to an improved abrading tool of the rotary type suitable for grinding, lapping, polishing and burnishing purposes.

BACKGROUND OF THE INVENTION

Conventional rotary abrading tools typically make use of a grindstone of ceramic, diamond, rubber or other abrasive of a suitable shape attached to a rotary shank, and the tip and other portions of the grindstone are used to grind, lap, polish or burnish surfaces as the tool is rotated by the shank and urged against the surfaces.

Such tools are customarily used for finishing machined surfaces or products and are also common in dental fields.

In other known finishing tools, the abrading member is a brush consisting of a multitude of densely packed bristles or wires which are mounted on a rotary hub or shaft so that their individual flexible tip portions are successively or continuously engageable with a surface to be treated to sweep over this surface as the hub or shaft supporting the brush is rotated.

These conventional abrading tools are unsatisfactory in material removal and low in operating efficiency. Additionally, they are found to be not readily applicable to diverse abradable sufaces or finishable sizes and configurations.

In the following description, reference to "abrading" will be understood to mean, generally, any surface treatment involving change in texture, usually with removal of small amounts of material. In particular it means any operation which involves grinding, lapping, polishing or burnishing or any combination of these operations.

OBJECT OF THE INVENTION

It is the principal object of the present invention to provide an improved abrading tool which affords an increased removal rate and/or improved finishing efficiency, yet permitting ready application to any of diverse grinding, lapping, polishing and burnishing requirements.

SUMMARY OF THE INVENTION

In accordance with the present invention there is provided an improved abrading tool which comprises a rotary shank and a plurality of elongate pieces fixedly mounted to said shank so as to individually project axially therefrom and extending so as to collectively form a forwardly converging body of revolution (at least in the rest state of the tool) rotatable about the axis of said shank, the pieces along the generatrices of said body under revolution serving as abrading surfaces.

Specifically, the elongate pieces are positioned in section in a row along a circle coaxial with the rotating shank, the number of the pieces on the circle not exceeding 20. The size in diameter or width of the preferably cylindrical elongate pieces generally ranges between 0.1 and 2 mm and preferably between 0.5 and 1 mm whereas the diameter of said circle should preferably range between 2 and 8 mm. The length l in mm of each of the elongate pieces should satisfy the relationship that l/D is at least 0.5 to 1 where D is the diameter of said circle or the diameter of the head portion of said shank.

In accordance with an important feature of the invention, the generatrices of the body of revolution collectively formed by the elongate pieces or the substantial outer lateral surfaces of the individual pieces whose one ends are held by the shank are used to tangentially bear against a workpiece surface to be treated. The individual elongate pieces which are so secured are resilient, stiff and yet when they are revolved with the rotation of the shank, at an operating speed, are allowed to expand toward their free ends or tips so that the body generatrix which is initially or in stationary (rest) state conical or of the configuration of a frustocone becomes cylindrical surfaces rapidly revolving. As a result, a continuous "beating" or "slapping" effect is created by the successive high-velocity or instantaneous tangential collisions consecutively brought about between the revolving elongate surfaces and the workpiece surface. With the rotation of the shank stopped, the working member resumes the original configuration of the forwardly converging body of revolution.

SPECIFIC DESCRIPTION

Figure 1A:
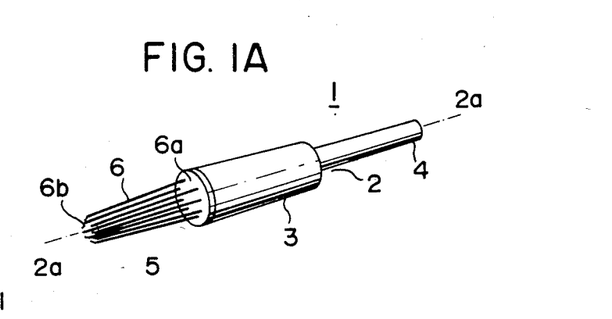
FIGS. 1A and 1B are diagrammatic perspective views of an abrasive tool according to the invention shown in stationary and rotating states, respectively.
Figure 1B:
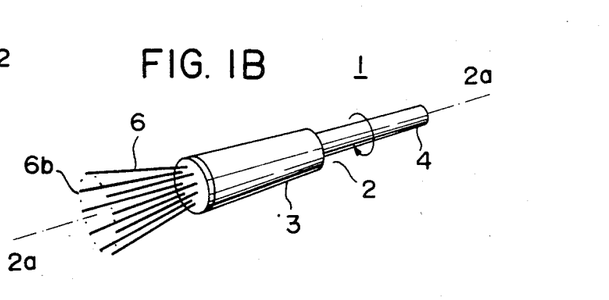

In FIGS. 1A and 1B an abrading tool embodying the present invention is illustrated in stationary and rotating states, respectively. The tool 1 has a shank 2 divided into cylindrical head portion 3 and a shaft 4 coaxially secured or integral therewith and a tool working member or body 5 comprising a plurality of elongate pieces 6 fixedly mounted to the head 3, preferably detachably through an arrangement which will be described. The shaft 4 is connected to a drive shaft of an operating motor 7 (FIG. 3) (e.g. via a chuck) for rotation of the tool working member 5.

The elongate pieces 6 are implanted in the cylindrical head 3 in a row along a circle shown at 6a on the end face of the head 3 so as to individually project therefrom in such a manner that they collectively form an axially converging body of rotation coaxial with the axis 2a of the shank 2 in the nonrotating or rest state.

Figure 15A:
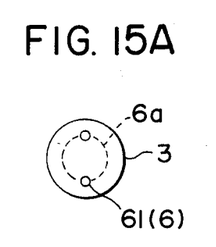
FIGS. 15A, 15B and 15C are end views of the holder portion of tools such as that shown in FIG. 14 and elsewhere to illustrate the distribution of the elongate working pieces and members.
Figure 15B:
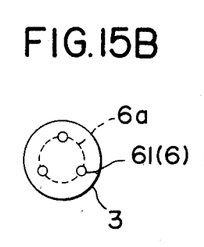
Figure 15C:
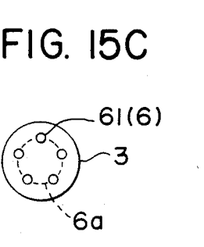

Elongate pieces 6 in relation to the head 3 and the imaginary circle 6a are shown to be fitted into the head in varying numbers of such pieces (FIG. 15) in angularly equispaced relationship about the tool axis.

Each of the elongate pieces 6 may be rod, wire or bristle composed of a substance selected from the group which consists of piano wire steel, mild steel, hardened steel, high-speed tool steel, stainless steel, brass, tungsten carbide, titanium carbide, tantalum carbide, titanium-nickel alloy, copper-beryllium alloy, iron, aluminum, nickel, tungsten, molybdenum, copper, copper-tin alloy, boron carbide, iron-chromium alloy, plastic, graphite and glass or any metal or alloy coated with a hard substance such as tungsten carbide, titanium carbide, tantalum carbide, boron carbide, silicon carbide, diamond and boron nitride (or any of the abrasive substances mentioned hereinafter) in a granular or nongranular form.

Thus a truly abrasive tool, which permits substantial amounts of material removal, can be provided with elongate pieces 6, each coated at least over part of its length with a hard substance, say diamond grits. The hard substance may be formed directly upon the substrate surface, e.g. by hard facing or crystallographic modification (for example the diffusion of carbon or nitrogen into the substrate) or may be applied by any method (e.g. electrodeposition) and bonded by any technique (including the use of bonding agents, sintering etc.).

Each elongate piece can be a sintered hard substance such as diamond or cubic boron nitride in a metal-powder matrix.

Nonmetallic elongate pieces, e.g. of plastic, glass or graphite, can have the abrasive grit imbedded therein.

The pieces 6 may each be either rounded or angular and are typically of a size in diameter between 0.1 and 2 mm and, preferably, between 0.5 and 1 mm. Such pieces may be bundled and assembled together with the head 3 so as to be arranged three to twenty in total number along the circle 6a which may then be of a diameter of 2 to 8 mm.

When the shaft 4 is rotated, the elongate pieces 6 revolve about the axis 2a. Then, as shown in FIG. 1B, the pieces 6 are forced radially outwardly toward their respective free ends so that their generatrices, originally defining a forwardly pointed cone or truncated cone (frustocone), forwardly expands to assume substantially a cylinder or a slight inwardly arcuate or straight cone forwardly or backwardly pointed.

By urging the revolving pieces 6 tangentially against a workpiece surface 8 (FIG. 3), the latter can be ground, lapped, polished or burnished as desired. The rate of revolution is chosen from the range between 500 and 50000 rpm with a range of 500 and 2000 rpm in a relatively low load operation and a range of 5000 to 50000 rpm in a relatively high load operation. The latter range can be used with elongated tool pieces 6 shaped to be angular in section where a substantial amount of stock is to be removed from the workpiece 8 with the tangential velocity of the revolving pieces 6 in the range between 1 and 15 m/sec.

In operation, the revolving pieces are successively brought into abrading contact with the surface 8. In each cycle of revolution, each piece 6 after coming out of contact with the surface 8 undergoes outward expansion and thereby picks up considerable kinetic energy which is released when it comes again in colliding contact with the surface 8 and tangentially beats or slaps the latt. This repeated "eating" or "slapping" effect produced by the revolving elongate pieces 6 is found to give rise to a markedly enhanced material removal which far exceeds that obtainable with a conventional "broom" type abrading tool which, as shown at 10 in FIG. 2, comprises a brush of densely packed wires or bristles 101 mounted on its shank and uses the brush end surfaces as the abrading face.

Figure 3:
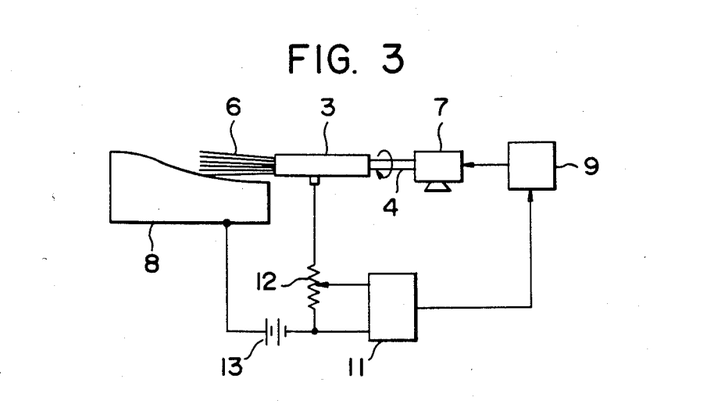
FIG. 3 is a diagrammatic view illustrating an adaptive abrading operation with a tool according to the invention.

In FIG. 3 there is shown a drive circuit system for operating the tool of the invention in accordance with one aspect thereof. In this system, the state of abrading contact between the revolving pieces 6 and the workpiece 8 is detected for control the operation of the motor 7. Thus, a power supply 9 for driving the motor 7 is provided with a control circuit 11 whose input terminals are tied across a sensing resistor 12 connected in series with a voltage source 13 and the workpiece 8 and also via a brush with the shank 2 rotating at an rpm in the range already specified. The relative displacement between the tool 1 and the workpiece 8 may either be performed manually or automatically. In the latter case, a numerical controller of any known configuration is advantageously provided to effect the relative displacement along a programmed feed path.

In the course of operation, change in contact pressure of the abrading tool working member 5 against the surface 8 will cause irregularity in abrasion which brings about irregularly finished or machine surfaces. This change is detected in the arrangement illustrated by monitoring electrical resistance between the contacting surfaces 6 and 8 measured as voltage drop at the resistor 12. As the contact resistance increases with the decrease of the urging pressure, the current from the source 13 passing through the resistor 12 is reduced and the voltage drop at the latter is lowered. Conversely, the increase contact pressure causes a decreased resistance which is measured as an increased voltage drop at the resistor 12. The control circuit 11 responds to change in voltage drop in the sensing resistor 12 to control the rpm of the motor 9. Increase in rpm causes an increase in the forwardly outward expansion of the revolving elongate pieces 6 which in turn results in an increased urging pressure thereby against the contacting surfaces 8 and vice versa.

In this manner, constancy in the abrading pressure between the tool working member 5 and the surface 8 required to obtain uniform "beating" or "slapping" effect is assured, this permitting material removal to continue with stability, with uniform surface finish over the entire machining area, at an increased finishing precision and performance for a given operation.

It should be noted that instead of its output rpm, the motor 7 may alternatively have its torque controlled to maintain the contact pressure constant. In this case, upon a change in the pressure measured the urging pressure can be increase and decreased with the increase and decrease of the torque respectively. Likewise, the torque of the motor 7 may be measured to monitor change in the contact pressure. Still alternatively, any other pressure sensing means such as piezoelectrical elements may be disposed at a suitable tool location to manifest variation in the contact pressure to control the rpm or torque of the drive motor 9 so as to hold the contact pressure constant.

While a satisfactory abrading tool operation can be performed by the abrading action of the elongate tool pieces 6 alone against the surface 8, any one or more auxilliary measures may be taken to achieve further enhanced machining results. For example, hard abrasive grit particles may be applied on the surfaces of the individual pieces 6 or alternatively used in suspension with a machining to cooling fluid to be supplied in the region between the working member 5 and the workpiece 8. Alternatively or in addition, an electrochemical machining current may be applied between the working member 5 and the workpiece 8 in the presence of an electrolyte so that material removal can be carried out by combination of electrolytic dissolution and mechanical abrading action.

EXAMPLE

Figure 2:
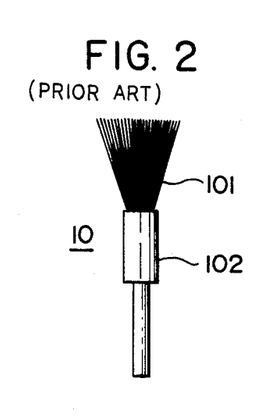
FIG. 2 is an elevational view diagrammatically illustrating a conventional "broom" type abrasive tool using a brush or wire or bristles.

A conventional practice requires 35 pieces of grindstone consisting of 80% by volume silicon carbide and the balance rubber to treat a cast body of nickel-manganese-iron alloy to modify its surface roughness from 25 $\mu$Rmax to 0.2 $\mu$Rmax, consuming approximately 3 hours. In accordance with an embodiment of the present invention, a tool member with five pieces of piano wire steel of 30 mm in length and 0.8 mm in diameter implanted equispacedly along a circle of 5 mm in diameter on the end of a shank revolved at 13,000 rpm requires only 12 minutes to accomplish the identical finishing oepration. Moreover, a single working member is found to be capable of yielding five similar pieces of finished product. In this case, diamond grit particles may be supplied to the region of the abrading interfaces. In a further comparison, a conventional "broom" type polisher consists of densely packed (more than 100 strands assembled together) wires as shown in FIG. 2 requires one and a half hours to achieve a single identical operation.

Figure 4A:
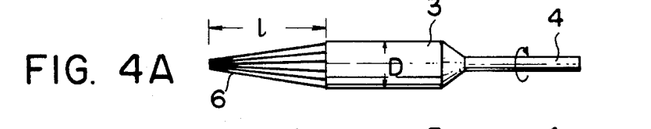
FIGS. 4A-4F diagrammatically illustrate abrasive tools with different forms of the working portion embodying the invention, in elevational views.
Figure 4B:
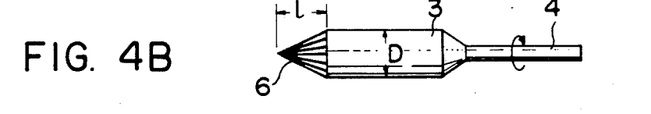
Figure 4C:
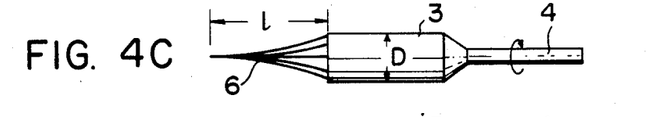
Figure 4D:
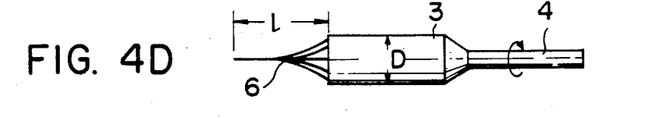
Figure 4E:
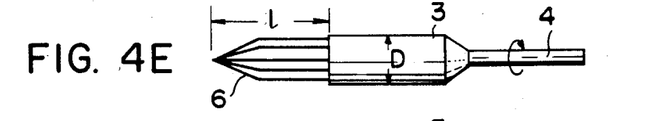
Figure 4F:
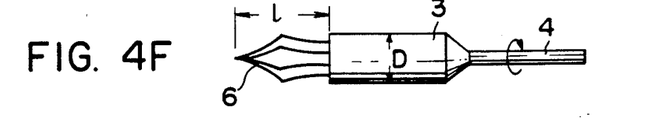

In FIGS. 4A-4F there are shown various forms of the tool working member 5 constituted by a plurality of elongate pieces which form a more or less "pencil" or "nib" shaped forwardly converging body of revolution. Specifically, the member 5 may be of truncated conical shape (FIG. 4A), of pointed conical shape (FIG. 4B), of inwardly arcuate conical shape (FIGS. 4C and 4D), and of combined shape of a cone and cylinder (FIGS. 4E and 4F).

In these embodiments, the circle (6a in FIG. 1) from which the pieces 6 individually project is substantially in registration with the diameter of the shank head portion 3. Accordingly, the length l of the tool working member 5 may have, with respect to said diameter D, the relationship: $l/D \geqq 0.5; \sim 1$.

Of various shaped members 5 illustrated a suitable one may be selected depending on the particular configuration and size of a surface to be treated. If the latter has a recess, the pointed tool member has a ready access thereto. With the rotation of the shaft 2, the pieces 6 are forced to expand toward their respective free ends as mentioned previously to effectively come in bearing contact with the wall of the recess.

Figure 5A:
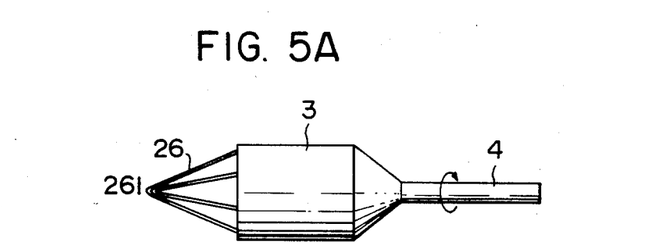
FIGS. 5A and 5B illustrate further embodiments of the working member of the tool according to the invention.
Figure 5B:
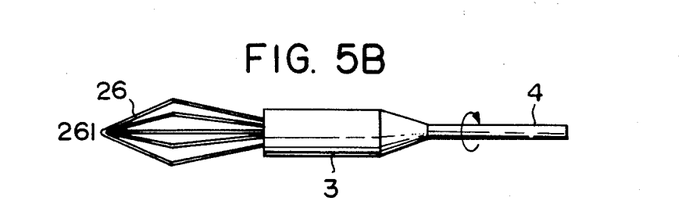

FIGS. 5A and 5B show modifications of the "nib" type abrasive tool member in which the elongate pieces 26 collectively forming the "nib" are connected with each other at the "pen point" 261 with each coupling forming a "V" shape specifically illustrated in FIGS. 6A-6E.

Figure 6A:
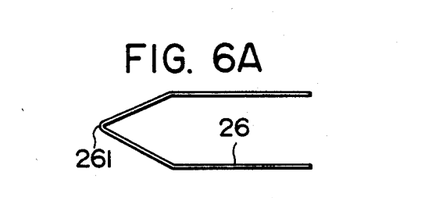
FIGS. 6A-6E illustrate other modifications of the type shown in FIGS. 5A and 5B.
Figure 6B:
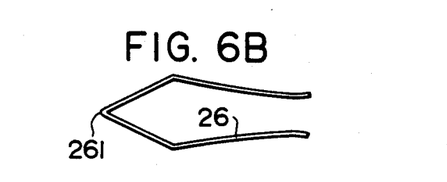
Figure 6C:
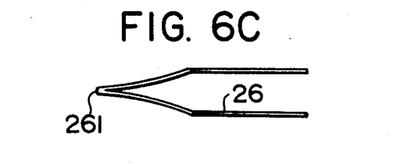
Figure 6D:
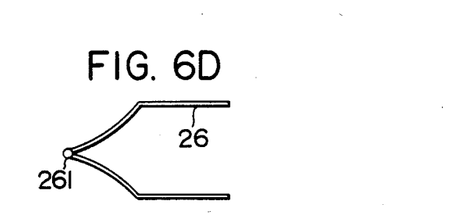
Figure 6E:
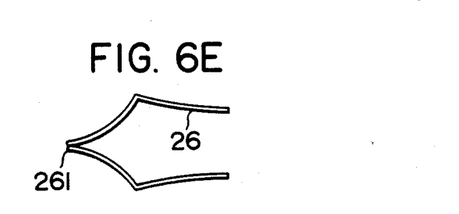

In the embodiments of FIGS. 6A-6C, single or unitary pieces are bent at their middle and shaped in section into any of the forms shown and then bundled. In the remaining embodiments, a plurality of bend-shaped pieces 26 are bonded together at their tips by welding, brazing, soldering etc. (FIG. 6D) or are merely resiliently brought together (FIG. 6E.). These assemblies with a pointed or converging tip as well are readily accessible to a recess and particularly suitable for a dental operation in a mouth to meet the requirement for safety.

At this point, it should be noted that when a tool according to the present invention is designed for dental use, elongate pieces constituting the working member are preferably composed of stainless steel or brass which is resistant to attack by a sterilizing fluid.

Figure 7:
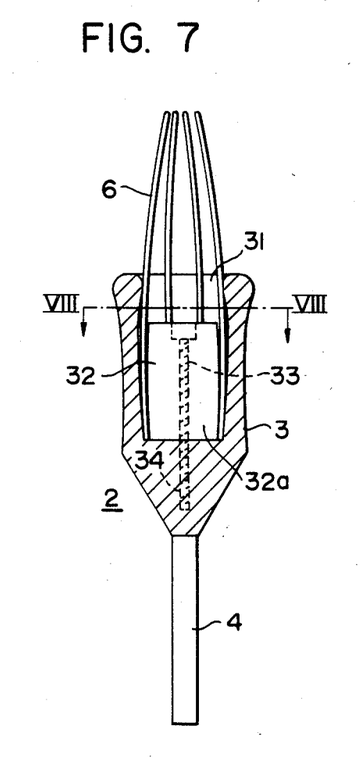
FIG. 7 is an axial cross-sectional view diagrammatically showing an arrangement for securing the working member to a shank of the tool according to the invention.
Figure 8:
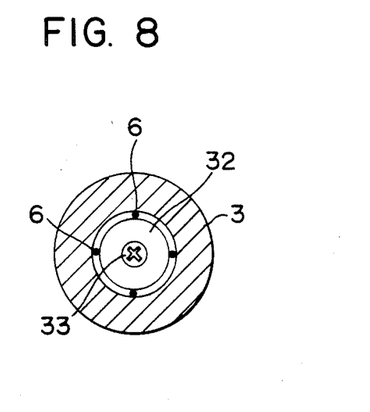
FIG. 8 is a cross-sectional view of the tool shown of FIG. 7 taken along the line VIII—VIII.
Figure 9:
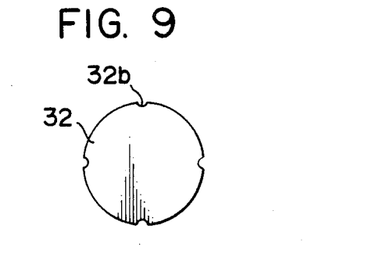
FIG. 9 is an end view of a core portion of the tool shown in FIGS. 7 and 8, drawn to an enlarged scale.

FIGS. 7, 8 and 9 show an arrangement whereby a plurality of elongate pieces 6 may be mounted securely upon or detachably connected to a shank 2 of the tool. Here, the head 3 of the shank 2 has a recess 31 coaxial with the shaft 4, the recess 31 being preferably tapered toward its upper end. Shown nested within the recess 31 is a plug member 32 formed centrally with an opening 32a for receiving a bolt 33 adapted to extend into the body of the head 32 coaxial therewith. The plug member 32 is shown further formed with axially extending grooves 32b equispaced on the periphery thereof correcponding in number to the pieces 6 to be mounted.

With the pieces 6 held respectively with grooves 32b of the plug member 32 against the wall of the tapered recess 31, the bolt 33 is secured to clamp the pieces 6 in place to the head 3.

Figure 10:
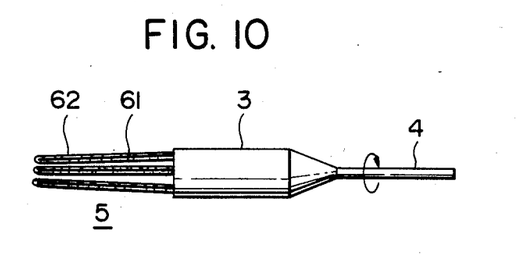
FIG. 10 is a side view of a tool constituting a further embodiment of the invention.
Figure 11:
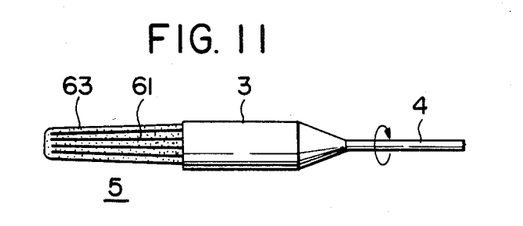
FIG. 11 illustrates a modified embodiment of the tool shown in FIG. 10.

FIGS. 10 and 11 show a modification of the tool working member 5 according to the invention in which the plurality of elongate pieces 61 are individually (FIG. 10) or as a whole (FIG. 11) coated with a natural or synthetic resin. So conditioned, the tool pieces 62 are rounded at their tip portions and such arrangements like those shown in FIGS. 5A to 6E are particularly advantageous, from the safety standpoint, for dental use in a mouth where a danager of possible wounding with a sharp tool is existent.

Figure 13A:
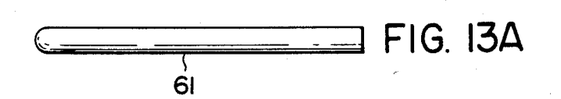
FIGS. 13A, 13B and 13C illustrate different elongate pieces formed with rounded tips in accordance with a further feature of the invention.
Figure 13B:
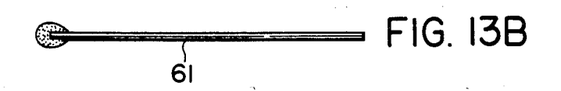
Figure 13C:
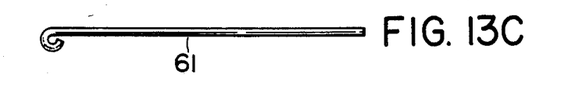

The arrangement of the tool member 5 in which the tip portions of elongate pieces 61 is rounded may also be embodied in the forms illustrated in FIGS. 13A to 13C. Thus, each tip of individual pieces 61 constituting the tool working member 5 may be made round by machining (FIG. 13A), applying a round deposit of metal, rubber, plastic, glass or ceramic thereon (FIG. 13B), or deforming (FIG 13C).

Figure 12:
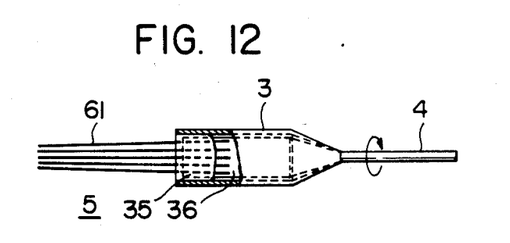
FIG. 12 is a side view (partly broken away) of the tool similar to those shown in the previous FIGURES and having a different fixture arrangement for securing the working member to the tool shaft.

A support structure for the working member 5 shown in FIG. 12 makes use of a core member 35 which is slidably received in the recess 31 formed in the head portion 3 of the shank 2 and is integral with or fixedly secured to the shaft 4. After positioning tool pieces 6 between the wall of the recess 31 and the core member 35, a bonding or soldering agent 36 is applied to fill the spaces within the recess 31 and set to firmly unite the pieces 6, the core member 35 and the head 3 together to permit the revolution of the tool member 5 attached to the shank 2. The attachment is readily decomposed as the replacement of pieces 6 is desired.

Figure 14:
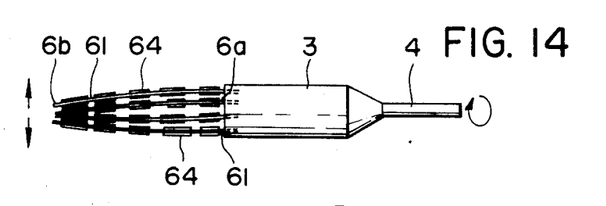
FIG. 14 is a side view of a further modification of a tool according to the invention and the best mode thereof.

In FIG. 14 there is shown a further modification of the abrading tool according to the invention in which each or at least in part of elongate pieces 61, e.g. a stainless-steel wire, plastic wire or glass wire, which is stiff and yet resilient, has a plurality of hard or abrasive chips 64, one spaced from the other, attached on the surface thereof, which chips are preferably composed of a ceramic. The chips 64 are also preferably elongated extending axially with the resilient supporting piece 61. A tool with the piece assembly 5 so constructed is particularly advantageous to form a dental tool.

Figure 16A:
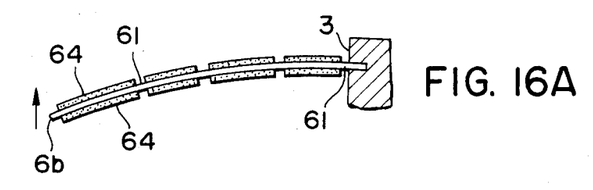
FIGS. 16A and 16B are longitudinal sections illustrating one of the elongate pieces of the tool of FIG. 14 as seen in its stationary and outwardly-spread (working) states, respectively.
Figure 16B:
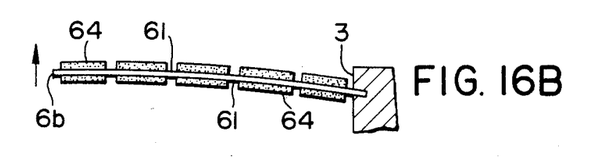

As in the embodiments which have been described, the piece assembly 5 has elongate pieces 61 firmly mounted equispacedly along a circle 6a to the holder 3 as shown in section in FIGS. 15A, 15B and 15C individually slightly inclined inwardly as shown in FIG. 16A so that with the shaft 4 rotated at an operating speed of 1000 to 20,000 rpm they resiliently expand outwardly toward the tips 66 thereof as shown in FIG. 16B so as to align substantially in parallel with the axis of the shaft 4 and holder 3.

Figures 17, 17A, 18, 19A, 19B, 19C:
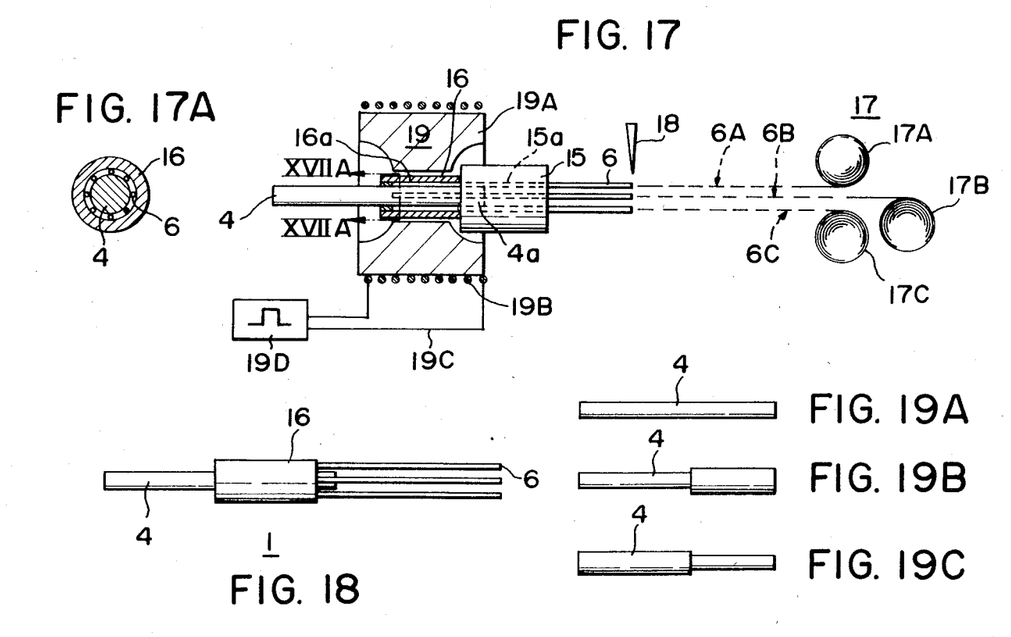
FIG. 17 is a sectional view diagrammatically illustrating an apparatus for forming an abrasive tool assembly according to the invention.
FIG. 17A is a cross section (take along line XVIIA—XVIIA of FIG. 17) of the tool as assembled in the apparatus of FIG.17.
FIG. 18 is a cross section illustrating a tool as assembled with the apparatus of FIG. 17.
FIGS. 19A, 19B and 19C show shapes of the shaft which can be used in assembling the tool with the apparatus of FIG 17.

In FIG. 17 there is shown a system for automatically or semi-automatically preparing or assembling an abrading tool 1 from a shaft 4 and a plurality of elongate pieces 6 which system constitutes a part of the present invention. The system makes use of a jig member 15 carried by a supporting structure (not shown) and having a cylindrical form open at both ends whose inner diameter is adapted to receive therein the end 4a of shaft 4 and a given number of elongate pieces 6 at their respective ends snugly between the shaft end 4a and the inner wall of the jig member 15a.

In the illustrated arrangement, the shaft end 4a is inserted from the left and the elongate pieces from the right into the jig member 15. Disposed coaxially with the shaft 4 and shown registered at its right end with the left end of the cylindrical jig 15 is a metal ring 16 which eventually forms the head of the tool and has an inner diameter substantially equal to or slightly larger than, the inner diameter of the cylinder 15 to accomodate the individual end portions of the elongate pieces 6 coming out of the cylinder 15 into a space defined between its inner wall 16a and the shaft 4.

Shown at the right side of the system is an elongate supply unit 17 comprising a plurality of supply drums 17A, 17B and 17C for individually feeding elongates 6A, 6B and 6C, respectively, through the jig member 15 into the ring 16 and each in position between the inner wall 16a thereof and the shaft 4. The elongates may be of any of the materials described previously, for example, stainless steel, piano-wire material, mild steel or hard alloy. In the path of the elongates 6A, 6B and 6 between the supply unit 17 and the jig member 15 there is provided a cutter 18 which may be operated upon a predetermined length of feed of the elongates 6A, 6B and 6C from the supply unit 17 to automatically cut them so that a set of elongate pieces 6 projected from the ring 16 uniformly by a predetermined length may be provided.

In this system, the metal ring 16 is disposed in a workable relationship with a magnetic pulse forming unit 19 comprising an annular field concentrator 19A coaxially surrounding the ring 16 and along its outer surface wound by an electromagnetic coil 19B. The coil 19B is energized via an operating switch 19C by a power supply 19D comprising a capacitor back which, when the switch 19C is closed, applies an impulsive electric current through the coil 19B to set up a magnetic field of high flux density about it.

The high-density field induces a current in the metal ring 16 disposed in the magnetic field and the interaction between the high-density magnetic field and the induced current in the metal ring 16 produces a resultant force impulse on the ring 16 which shapes it and causes it to be shrunken instantaneously thereby clamping the ring 16, the end portions of the elongate pieces 6 and the shaft 4 together.

A completed assembly is shown in FIG. 18. It should be noted that the shaft 4 may have any of the forms shown in FIGS. 19A, 19B and 19C. This system allows volume production with a high precision and reproduction rate of abrading tools 1.

Figure 20:
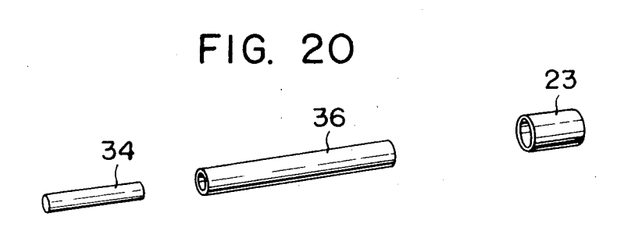
FIG. 20 illustrates another apparatus for making an abrading tool according to the invention.
Figures 21, 22A, 22B:
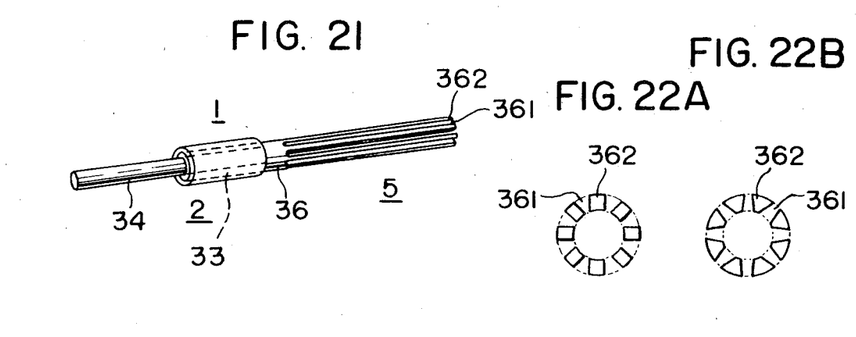
FIG. 21 is a diagrammatic sectional view of the tool made with the system of FIG. 20.
FIGS. 22A, 22B and 22C illustrate in section various configurations of the elongate pieces or members which can be used in the tool of FIG. 21.

Another method of preparing an abrading tool 1 according to the invention makes use of an elongate pipe 36, a shaft 34 and a clamping pipe 33 as shown in FIGS. 20 and 21. In this embodiment, the elongate pipe 36 is formed with a plurality of equispaced and axially extending slits 361 cut from one end thereof into a given substantial length.

As the result of such toothed formation, a plurality of annularly arranged, equispacedly and lengthwise extending elongate pieces 362 projecting uniformly in parallel with one another from the other end portion are provided which, coupled to the end portion which forms a support member, may effectively serve as abrasive working elements as in the previous embodiments with a substantially identical function.

After formation of teeth 361, 362, the toothed portion of the pipe 36 may be mechanically deformed to forwardly converge and the shaft 34 is inserted into the machined pipe 36 from the unmachined end thereof into position and the clamping pipe 33 is fitted over the untoothed portion of the pipe 36 to tightly hold the same in which the shaft 34 is fixedly received as shown in FIG. 21.

Advantageously, fixing between the shaft 34 and the pipe 36 and also between the latter and the clamping pipe 33 may be effected with the aid of an adhesive, e.g. a phenol-type or epoxy-type bonding agent or, alternatively, welding, brazing, or soldering may be used.

Figure 22C:
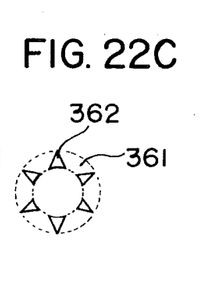

The structure of the working member 5 just described has advantages over the use of separate elongate pieces assembled together in that it permits easy production and working with revolution with an increased precision. Material forming the pipe 36 may advantageously be stainless steel, mild steel, hardened steel, copper, brass or hard alloy. FIG. 22 illustrates modifications of a pipe 36 formed with slits of various shapes in cross section to provide elongate pieces of desired section (FIGS. 22A, 22B and 22C).

Figure 23A:
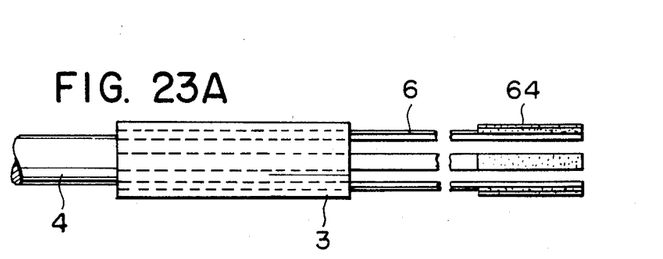
FIGS. 23A and 23B show embodiments similar to that illustrated in FIG. 14 but having a continuous abrasive layer extending over the tip portion of each elongate piece.
Figure 23B:
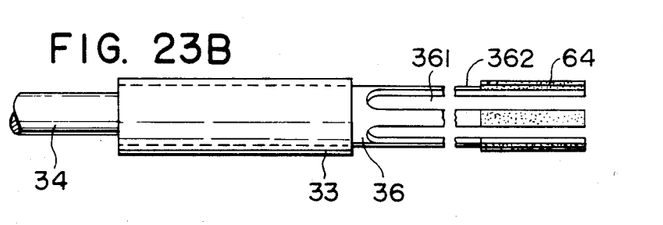

FIGS. 23A and 23B show further modified embodiments of the present invention wherein a thin abrasive layer 64 is applied to the tip portion of each of elongate pieces 6 originally separate and assembled together (FIG. 23A) or elongate pieces 36 provided by the toothed formation (FIG. 23B). The tooth formation 361, 362 may be provided in the manner as has been described. The abrasive layer may contain abrasive grits of diamond, $Al_2O_3$, BN, $Zr_2O_3$, $SiO_2$, SiC, WC, TiC, TaC etc., which may be bonded together by electrodeposition, sintering, welding or adhesive bonding.

Figure 24:
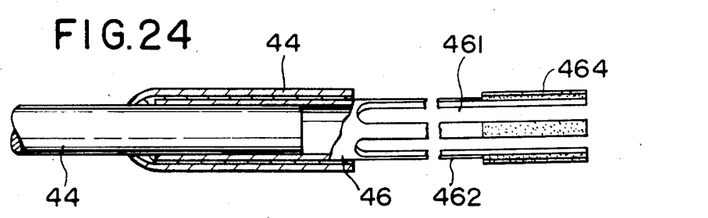
FIG. 24 illustrates in section a system for assembling and uniting the shaft, elongate pieces or members and the casing.

FIG. 24 shows in cross section an abrading tool assembly comprising a tubular member 46 formed with toothed elongate formations 461, 462 at one end and having a shaft 44 received therein at the other end with each tip of elongate projections having an abrasive layer 464 of composition described. In this case, the support portion of the pipe 46 is enclosed with a tubular casing 44 with the intervening space filled with an adhesive to unite the casing 44, the pipe 46 and the shaft together.

There is thus provided an improved abrading tool of rotary type which affords an increased removal rate of finishing efficiency and which is diverse in its applications.

I claim:

1. A machine comprising:
   a tool for treating a workpiece comprising a a rotary shank and a plurality of elongated pieces fixed at corresponding ends to said shank so as to individually project axially therefrom and extending so as to collectively form, when the shank is not in rotation, a forwardly converging inactive body of revolution substantially centered on the rotary axis of said shank, said pieces being stiff and resilient and having workpiece-treating surfaces along a length thereof; and
   a motor connected to said shank for rotating said tool at a speed sufficient with respect to the stiffness of said pieces such that the pieces collectively form an active body of revolution centered on the rotary axis of said shank and with free ends of said pieces spread away from one another and from their positions in said inactive body solely by the centrifugal force of said rotation, said active body of revolution having a generatrix, said surfaces of said pieces along said generatrix of said active body of revolution when said motor rotates said shank serving as an abrading or burnishing means slapping at a workpiece when said tool is engaged laterally by a workpiece.

2. The machine defined in claim 1 wherein each of said elongated pieces has a hard substance exposed at said surface and sintered in a metal matrix.

3. The machine defined in claim 2 wherein said substance is abrasive.

4. The machine defined in claim 1 wherein each of said elongated pieces is comprised at least in part by a substance selected from the group which consists of piano wire steel, high-speed tool steel, stainless steel, mild steel, brass, tungsten carbide, titanium carbide, tantalum carbide, titanium-nickel alloy, copper-beryllium alloy, iron, aluminum, nickel, tungsten, molybdenum, copper, copper-tin alloy, boron carbide, iron-chromium alloy, plastic, graphite, and glass.

5. The machine defined in claim 4 wherein each of said elongated pieces is of a transverse size between 0.1 and 2 mm.

6. The machine defined in claim 5 wherein said size is between 0.5 and 1 mm.

7. The machine defined in claim 6 wherein 3 to 20 such pieces are provided in said tool and are disposed along a circle.

8. The machine defined in claim 7 wherein said circle has a diameter between 2 and 8 mm and said pieces individually project by a length l such that the ratio l/D is at least 0.5.

9. The machine defined in claim 2 wherein said hard substance is selected from the group which consists of diamond, boron nitride, a ceramic, silicon carbide and a metal carbide.

10. A machine including a tool for frictional treatment of a workpiece surface comprising a rotary shank and a plurality of flexible elongate pieces of angular cross section fixed at corresponding ends to said shank so as to individually project axially therefrom and extending so as to collectively form a forwardly converging body of revolution in a rest position of said tool rotatable about the axis of said shank, said body expanding upon rotation and having a generatrix, the generatrix of said body of revolution serving as an abrading means, said elongate pieces being composed of at least one substance selected from the group consisting of piano wire steel, a mild steel, hardened steel, high-speed tool steel, stainless steel, brass, tungsten carbide, titanium carbide, tantalum carbide, titanium-nickel alloy, copper-beryllium alloys, iron, aluminum, nickel, tungsten, molybdenum, copper, copper-tin alloys, boron carbide, iron-chromium alloy, plastic, graphite and glass, said elongate pieces each having a transverse size between 0.1 and 2 mm, a motor connected to said shank for rotating same at a speed between 500 and 50,000 rpm, means for detecting contact pressure between said elongate pieces and a workpieces to be treated, and means responsive to said detecting means for controlling said motor so as to maintain said contact pressure substantially constant.

11. The machine defined in claim 10 wherein said detecting means comprises means for sensing electrical resistance between said elongate pieces and said workpieces.

12. The machine defined in claim 10 wherein said controlling means is adapted to control the rate of rotation of said motor.

13. A machine including:

an abrading tool comprising a rotary shank and a plurality of elongated pieces fixed at corresponding ends to said shank so as to individually project axially therefrom and entending so as to collectively form, when the shank is not in rotation, a forwardly converging inactive body of a revolution substantially centered on the rotary axis of said shank and, when the shank is in rotation, to collectively form an active body of revolution centered on the rotary axis of the shank and with free ends expanded away from one another from their positions when the shank is not in rotation, said active body of revolution having a generatrix, the generatrix of said active body of revolution when the shank is in rotation serving as an abrading or burnishing means, said elongate pieces being each of a transverse size between 0.1 and 2 mm;

drive means including a motor connected to said shank for rotating same at a speed between 500 and 50,000 rpm; and means for detecting contact pressure between said elongate pieces under revolution and a workpiece to be treated, and means responsive to said detecting means for controlling said motor so as to maintain said contact pressure substantially constant.

14. The machine defined in claim 13 wherein said detecting means comprises means for sensing electrical resistance between said elongate pieces and said workpiece.

15. The machine defined in claim 13 wherein said controlling means is adapted to control the rate of rotation of said motor.

* * * * *